(12) United States Patent
Dennis

(10) Patent No.: US 11,065,452 B2
(45) Date of Patent: Jul. 20, 2021

(54) VENTRICULAR TACHYCARDIA STORM ANALYSIS AND VENTRICULAR TACHYCARDIA STORM INTERVENTION METHOD AND SYSTEM

(71) Applicant: PACESETTER, INC., Sylmar, CA (US)

(72) Inventor: Malcolm Dennis, Surrey Hills (AU)

(73) Assignee: PACESETTER, INC., Sylmar, CA (US)

( * ) Notice: Subject to any disclaimer, the term of this patent is extended or adjusted under 35 U.S.C. 154(b) by 304 days.

(21) Appl. No.: 15/585,966

(22) Filed: May 3, 2017

(65) Prior Publication Data

US 2018/0318588 A1 Nov. 8, 2018

(51) Int. Cl.
| | |
|---|---|
| *A61N 1/365* | (2006.01) |
| *A61N 1/362* | (2006.01) |
| *A61N 1/37* | (2006.01) |
| *A61N 1/372* | (2006.01) |
| *A61N 1/39* | (2006.01) |
| *A61B 5/00* | (2006.01) |
| *A61B 5/361* | (2021.01) |
| *A61B 5/363* | (2021.01) |

(52) U.S. Cl.
CPC ........ *A61N 1/36514* (2013.01); *A61B 5/4836* (2013.01); *A61N 1/3621* (2013.01); *A61N 1/371* (2013.01); *A61N 1/37252* (2013.01); *A61N 1/3925* (2013.01); *A61N 1/3987* (2013.01); *A61N 1/39622* (2017.08); *A61B 5/361* (2021.01); *A61B 5/363* (2021.01)

(58) Field of Classification Search
None
See application file for complete search history.

(56) References Cited

U.S. PATENT DOCUMENTS

| | | | |
|---|---|---|---|
| 8,170,668 B2 * | 5/2012 | Ettori | A61B 5/0464 607/14 |
| 8,391,980 B2 | 3/2013 | Bornzin et al. | |
| 8,831,747 B1 | 9/2014 | Min et al. | |
| 9,216,285 B1 | 12/2015 | Boling et al. | |
| 9,232,485 B2 | 1/2016 | Wu et al. | |
| 2003/0191403 A1* | 10/2003 | Zhou | A61B 5/0464 600/515 |

* cited by examiner

*Primary Examiner* — Michael W Kahelin
*Assistant Examiner* — Elizabeth K So
(74) *Attorney, Agent, or Firm* — The Small Patent Law Group LLC; Dean D. Small

(57) ABSTRACT

Methods, devices and program products are provided. The method is under control of one or more processors within an implantable medical device (IMD), obtains cardiac signals that comprise candidate episodes over a period of time and updates an episode count and episode density clock based on the candidate episodes within the period of time. Further, the method determines whether the candidate episodes are indicative of a ventricular storm arrhythmia based on the episode count and episode density clock, identifies a storm origin characteristic of interest preceding onset of the candidate episodes and directs the IMD to perform a storm intervention based on the identifying operation.

11 Claims, 10 Drawing Sheets

VENTRICULAR TACHYCARDIA STORM ANALYSIS AND VENTRICULAR TACHYCARDIA STORM INTERVENTION METHOD AND SYSTEM

BACKGROUND

Embodiments of the present disclosure generally relate to methods and devices to terminate ventricular tachycardia and/or ventricular fibrillation storm.

Ventricular tachycardia (VT) and ventricular fibrillation (VF) (collectively VT/VF) storm occurs in 10-20% of recipients of implantable cardioverter defibrillators (ICD). As one example, a VT/VF storm may be characterized by a predetermined number of episodes of VT/VF within a predetermined period of time (e.g., 3 or more episodes of VT/VF within 24 hours). As another example, aggressive VT/FT storm may include 20-50 VT or VF episodes in a space of a few hours. At least one prior review of VF frequency during storm in patients having an implantable cardioverter defibrillator has shown aggressive clustering of VT and/or VF episodes, with a mean of 25+/−82 episodes per storm.

When a VT or VF episode is experienced, the ICD delivers a corresponding therapy. During VT/VF storm, the ICD will deliver a corresponding therapy in connection with all (or at least several) of the VT or VF episodes experienced during the VT/VF storm which draws down battery power. As one extreme example, an ICD may deliver over 3000 shocks during a single VT storm. Accordingly, patients who experience excessive VT/VF storm cycle through the ICD battery faster than in most patients and may need to replace an ICD more frequently than originally predicted.

SUMMARY

In accordance with embodiments herein a method is provided. The method is under control of one or more processors within an implantable medical device (IMD), obtains cardiac signals that comprise candidate episodes over a period of time and updates an episode count and episode density clock based on the candidate episodes within the period of time. Further, the method determines whether the candidate episodes are indicative of a ventricular storm arrhythmia based on the episode count and episode density clock, identifies a storm origin characteristic of interest preceding onset of the candidate episodes and directs the IMD to perform a storm intervention based on the identifying operation.

Optionally, the method may further detect, as the candidate episodes, at least one of VT episodes or VF episodes. The determining operation may comprise determining whether a predetermined number of the at least one of VT episodes or VF episodes occur within a predetermined period of time. The method may determine the storm origin characteristic of interest from one or more events that precede onset of the corresponding candidate episodes. The one or more events may precede onset of the corresponding candidate episodes by a predetermined number of events that is between 3 and 6. The method may further, for each candidate episode, determine a candidate origin characteristic of interest preceding the corresponding candidate episode.

Optionally, the candidate origin characteristic of interest represents at least one of a beat to beat interval or a heart rate. The directing operation may include directing the IMD to deliver an intervention therapy based on the storm origin characteristic of interest. The intervention therapy may represent a pacing therapy having a pacing rate that is based on the storm origin characteristic of interest. The candidate origin characteristic of interest may represent at least one of a beat to beat interval or a heart rate. The pacing rate may be set a predetermined amount greater than the at least one of a beat to beat interval or a heart rate. The directing operation may include at least one of i) providing a physical indication to a patient having the IMD or ii) transmitting a storm indication to an external device.

In accordance with embodiments herein a system is provided. The system comprises an implantable medical device. The implantable medical device comprises memory to store cardiac signals that comprise candidate episodes over a period of time. The memory stores program instructions. The implantable medical device further comprises a processor that, when executing the program instructions, updates an episode count and episode density clock based on the candidate episodes within the period of time, determines whether the candidate episodes are indicative of a ventricular storm arrhythmia based on the episode count and episode density clock, identifies a storm origin characteristic of interest preceding onset of the candidate episodes and directs the IMD to perform a storm intervention based on the identifying operation.

Optionally, the processor, when executing the program instructions, may further detect, as the candidate episodes, at least one of VT episodes or VF episodes. The processor, when executing the program instructions, may further determine whether a predetermined number of the at least one of VT episodes or VF episodes occur within a predetermined period of time. The processor, when executing the program instructions, may further determine the storm origin characteristic of interest from one or more events that precede onset of the corresponding candidate episodes. The one or more events may precede onset of the corresponding candidate episodes by a predetermined number of events that is between 3 and 6.

Optionally, the processor, when executing the program instructions, may determine, for each candidate episode, a candidate origin characteristic of interest preceding the corresponding candidate episode. The candidate origin characteristic of interest may represent at least one of a beat to beat interval or a heart rate. The IMD may comprise electrodes which may provide therapy. The processor, when executing the program instructions, may direct the IMD to deliver an intervention therapy through the electrodes. The intervention therapy may be based on the storm origin characteristic of interest. The system may further comprise an external device. The IMD may transmit a storm indication to an external device.

In accordance with embodiments herein, methods and systems are provided to monitor for a mechanism of VT and/or VF storm and to intervene automatically. A process is described to arrest VT/VF storm, activate alerts and notify individuals to provide prompt medical attention. The process activates intervention once a select episode density has been reached. Thus, VT storm may be terminated immediately rather than continuing until definitive medical management is undertaken.

The methods and systems intervene to terminate VT storm using a number of physician controlled variables. A process identifies a VT/VF storm when a predetermined episode density occurs, for example when a select number of VT/VF episodes occur within a select time frame (e.g., 5 episodes in 6 hours, 10 episodes in 10 hours). When the predetermined episode density is reached, a VT/VF storm analysis is performed in search of a storm origin. The VT/VF storm analysis determines whether all (or a predetermined number of) VT/VF episodes emerge from (follow) a common characteristic, such as a uniform preceding cycle length or heart rate range. For example, the heart rate range may be X+/−5 events per minute or another physician selected uniformity range. When a common characteristic is identified, the characteristic is labeled as a storm origin characteristic (e.g., a storm origin cycle length, or storm origin heart rate); a VT storm intervention therapy is applied based on the storm origin characteristic.

In accordance with embodiments herein, an implantable medical device (IMD) implements a VT storm intervention therapy, in which a select pacing rate is applied for a selected duration, such as 20 events per minute faster, or 20 percent faster than the identified storm origin cycle length. A maximum (capped) intervention heart rate may be selected by the physician in light of known cardiac factors (e.g., 100-120 events per minute). The storm intervention therapy is applied until time out of a select duration or the therapy is deactivated during a programmer session. The IMD may produce various outputs in connection with a storm intervention process. For example, the IMD may provide, as an output, an activation of a patient vibratory notification and/or transmit an alert to a bedside monitoring system (e.g., the Merlin.NET™ network) to prompt the patient to seek medical attention for management of the storm episodes.

A VT storm intervention therapy may represent an emergency strategy with multiple physician-selected parameters and boundaries of scale. The emergency strategy may be applied when analysis of the current VT storm confirms that the storm origin characteristic represents a treatable onset mechanism.

In accordance with embodiments herein, the storm origin characteristic is determined based on cardiac signals. During a VT/VF storm, cardiac signals (preceding the VT/VF episodes) may reveal that episodes of VT or VF emerge from a common characteristic of pre-episode events, such as uniform narrow heart rate range, or from a similar, repeating cycle length. Optionally, the common characteristic may represent a pause duration within long-short, or short-long-short sequences. When the pre-episode cardiac signals indicate that episodes of VT or VF emerge from one or more common characteristics, then a rate (or pause) dependence (or contribution) is implicated. Embodiments herein apply a physician-selected pacing rate that is defined based on the common characteristic. For example, a pacing rate increase may be applied for a selected duration when the onset of VT/VF episodes within a storm are demonstrated to occur from a uniform preceding cycle length (rate or pause). Optionally, a predetermined (e.g., emergency) intervention may be applied based on multiple physician-selected variables (e.g., a set pacing rate) that define operation of the IMD during VT/VF storm. The predetermined intervention may be applied when the onset of episodes is demonstrated to emerge from a uniform rate or from a pause within long-short or short-long-short sequences.

In accordance with embodiments herein, methods and systems are described that reject or void defining storm intervention therapy on arrhythmia transition events, such as unclassified or mis-classified initial VT or VF events. Instead, the systems and methods define intervention therapy on the true pre-tachycardia heart rate or pause duration.

DETAILED DESCRIPTION

Figure 1:
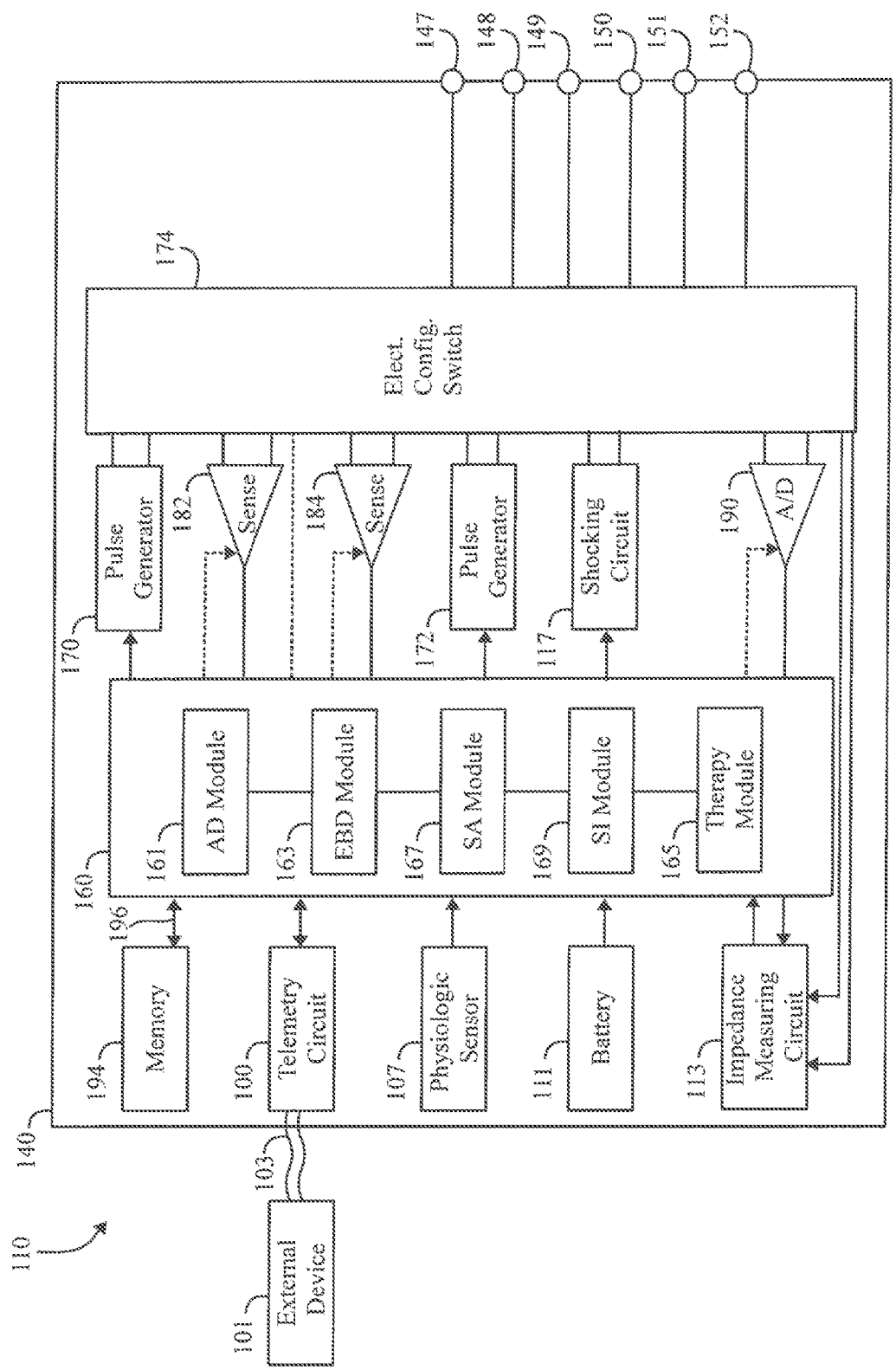
FIG. 1 illustrates a block diagram of an IMD which may represent a leadless IMD and/or a subcutaneous IMD capable of performing the methods described herein and of treating ventricular storm arrhythmias.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. in other instances, well-known structures, materials, or operations are not shown or described in detail to avoid obfuscation. The following description is intended only by way of example, and simply illustrates certain example embodiments.

Definitions

The terms "VT storm", "YE storm", "VF storm episode", "VT storm episode", and generally "VT/VF storm" and "storm", shall refer to a condition in which a patient, with an IMD, experiences multiple episodes of ventricular tachycardia and/or ventricular fibrillation within a predetermined period of time. VT/VF storm may also be indicated by a patient having an implantable cardioverter defibrillator who is shocked multiple times within the predetermined period of time. As examples, VT/VF storm may manifest as three or more episodes of VT/VF within 24 hours. More aggressive examples of storm may include 20-50 VT or VF episodes in the span of a few hours.

The term "ventricular storm arrhythmia" shall refer to ventricular tachycardia storm and/or ventricular fibrillation storm.

The term "storm origin" refers to a cardiac event, preceding a VT/VF storm, that has one or more characteristics i) represent a contributing factor to cause the VT or VF storm, and/or ii) represents an intervention factor that can be utilized to stop and/or otherwise reduce a frequency of VT or VF episodes. The storm origin represents a pre-tachycardia event.

The term "origin lag" refers to a number of events (e.g., paced and/or sensed events) or time duration that occurs between an episode origin and subsequent detection/identification of onset of a VT/VF episode. For example, an episode origin may precede the classification of the corresponding VT/VF episode by an origin lag of 3-6 paced/sensed events.

The terms "tachycardia binned event", "TACH binned event", "fibrillation binned event" and "FIB binned event" shall refer to the first event that is identified and declared as a tachycardia event or a fibrillation event within a VT or VF episode.

The terms "binned" and "binning" refer to a designation or marker determined by various algorithms implemented by an IMD in connection with classifying different types of cardiac events. A binned event may correspond to a normal/physiologic cardiac event or an abnormal cardiac event indicative of an arrhythmia. For example, a normal sinus sensed event may be binned/marked as a ventricular sensed event, an atrial sensed event and the like. As another example, a paced event may be binned/marked as a ventricular paced event, an atrial paced event and the like. In connection with embodiments herein, events associated with ventricular tachycardia and ventricular fibrillation are binned/marked as a "tachycardia binned event", "TACH binned event", "fibrillation binned event" or "FIB binned event". Is it is recognized that not every cardiac event will be binned/marked, instead, some cardiac events may be indeterminate and thus processed as "un-binned" or "unmarked" cardiac events. Cardiac events that are un-binned are indicated in the figures with a dash "-". Further, it is recognized that some cardiac events may be binned or marked incorrectly. For example, a cardiac event may be binned/marked as a normal sinus event, referred to as "binned as sinus", even though the cardiac event may be an arrhythmia transition event at a beginning of a VT or VF episode. The term "arrhythmia transition event" and "AE event" shall refer to events occurring between a storm origin event and the first TACH or FIB binned event in a VT/VF episode. For example, 1-5 AE events may occur between the storm origin event and the first TACH or FIB binned event. The terms "beat" and "event" are used interchangeably.

Storm Underpinning

Next, a general discussion of storm is provided. An episode of VT or VF is initiated when a combination of contributing mechanisms overlap in a particular manner. Examples of the combination of contributing mechanisms include refractory duration, temporal or spatial (transmural) dispersion of refractoriness, conduction velocity, and HR (or preceding cycle length). Each of the foregoing contributing mechanisms occurs within a corresponding critical range(s) and interact with each other to produce the VT or VF episode and a VT/VF storm. Critically timed premature ventricular contractions (PVCs) may also play a role in VT/VF aetiology. VT or VF storm is an uncommon occurrence.

In patients with recurrent VT or VF, the cardiac event pattern preceding VT/VF episode onset is frequently reproducible. Recurrent VT or VF episodes may be considered a VT/VF storm when the episode frequency reaches a selected value. Frequently recurrent episodes may occur when there is a sustained alignment (e.g., a critical alignment) of contributing factors for VT or VF onset, and the alignment of the contributing factors persists for a period of time, VT/VF storm may be characterized as mechanistic behavior rather than random behavior, where the mechanistic behavior includes one or more contributing factors that have varied sufficiently to allow the interplay with the other factors to enable continued re-expression as VT or VF.

The heart rate may be modulated in connection with VT/VF storm intervention. An effectiveness of heart rate modulation to stop VT/VF storm may vary, based in part on a type/pattern of episode sequence that precedes the VT or VF episodes. For example, heart rate modulation may exhibit one level of effectiveness in connection with storm preceded by long-short (LS) and short-long-short (SLS) sequences, as compared to storm preceded by other types of sequences. When VT or VF storm is preceded by LS or SLS sequences, elevation of the heart rate in part abolishes the 'long' interval between cardiac events, and changes the rate dependence of the contributory factors. Removing the long interval removes a foundation of the mechanism from which certain types of storm originate. In Brugada syndrome and idiopathic VF, pauses and bradycardia may accentuate J wave amplitude and/or the ST elevation of early repolarization, both of which may increase susceptibility to VT and VF, increased heart rates lessen these amplitude accentuation and repolarization abnormalities and can interrupt storm.

In some instances, such as monomorphic ventricular tachycardia, a pause- or preceding cycle length-dependence is less clear cut, yet the same contributing factors are operational (refractoriness, dispersion of refractoriness, conduction velocity and preceding cycle length) When these factors overlap in certain manners, VT occurs. When the factors do not overlap in the certain manner, VT does not occur. Hence, heart rate is a direct contributing factor, as well as an indirect contributing factor through the effect of heart rate refractoriness (and therefore re-entry and triggered activity). In accordance with embodiments herein, the heart rate is treated as a contributing factor to storm origin, and heart rate is utilized as a potential target for interrupting VT storm.

Implantable Medical Device

FIG. 1 illustrates a block diagram of an IMD 110 which may represent a leadless IMD, an IMD coupled to one or more leads, and/or a subcutaneous IMD capable of performing the methods described herein and of treating ventricular storm arrhythmias, as well as one or both of fast and slow arrhythmias with stimulation therapy, including cardioversion, defibrillation, and pacing stimulation. Non-limiting examples of IMDs include a cardioverter-defibrillator, cardiac rhythm management device, and defibrillator, whether utilizing leads or leadless. For example, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device and Method Including The Same", which are hereby incorporated by reference. Additionally or alternatively, the IMD may include one or more structural and/or functional aspects of the device(s) described in U.S. Pat. No. 8,391,980 "Method and System For Identifying A Potential Lead Failure In An Implantable Medical Device" and U.S. Pat. No. 9,232,485 "System And Method For Selectively Communicating With An Implantable Medical Device", which are hereby incorporated by reference. While a particular multi-chamber device is shown, this is for illustration purposes only. It is understood that the appropriate circuitry could be duplicated, eliminated or disabled in any desired combination to provide a device capable of simply monitoring impedance and/or cardiac signals, and/or treating the appropriate chamber(s) with cardioversion, defibrillation and pacing stimulation.

The housing 140 for the stimulation IMD 110 is often referred to as the "can", "case" or "case electrode" and may be programmably selected to act as the return electrode for some or all sensing modes. The housing 140 may further be used as a return electrode alone or in combination with one or more other electrodes. The housing 140 farther includes a connector (not shown) having a plurality of terminals 147-152. To achieve sensing, pacing and shocking in connection with desired chambers of the heart, the terminals 147-152 are selectively connected to corresponding combinations of electrodes and/or different portions of the device housing 140.

The IMD 110 includes a programmable processor 160 that controls the various modes of sensing and stimulation therapy. The processor 160 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The processor 160 includes the ability to process or monitor input signals (data) as controlled by a program code stored in memory. The details of the design and operation of the processor 160 are not critical to the present invention. Rather, any suitable processor 160 may be used.

The processor 160 includes inputs that are configured to collect cardiac signals associated with electrical or mechanical behavior of a heart over multiple cardiac cycles. The cardiac signals may be IEGM signals from the cardiac sensing circuits 182, 184 representative of electrical behavior of the heart. The circuits 182, 184 may provide separate, combined, composite or difference signals to the processor 160 representative of the sensed signals from the electrodes. Optionally, the cardiac signals may be the output of the A/D circuit 190 that are representative of electrical behavior of the heart. The cardiac signals may be the output of the physiologic sensor 107 that are representative of mechanical behavior.

The processor 160 includes an arrhythmia detection (AD) module 161, an event binning/marker (EMD) module 163, a therapy module 165, a storm analysis (SA) module 167, and a storm intervention (SI) module 169 (among other things). The AD module 161 is configured to analyze cardiac signals to identify arrhythmias of interest, such as ventricular arrhythmias (VT or VF), as well as atrial arrhythmias. The EMD module 163 is configured to record markers or bin classifications in connection with each cardiac event, such as ventricular paced (VP) events, atrial paced (AP) events, ventricular sensed (VS) events, atrial sensed (AS) events, tachycardia (T) or (T2) events, fibrillation (F) events and the like. In the event that a particular cardiac event is not identified, the cardiac event may be labeled with a dash "-". The markers/bin classifications are noted in the FIGS. 3A-3E in connection with example patterns that contribute to storm. The SA module 167 performs storm analysis as described herein. The SI module 169 performs storm intervention as described herein. The therapy module 165 is further configured to deliver therapy based on, among other things, the cardiac signals, storm analysis, and the storm intervention.

The processor 160 is configured to perform program instructions to, among other things, identify whether a uniform pause or heart rate precedes repeated VT onset and if so, apply a select, capped, pacing rate increase. The pacing rate increase is set to be sufficient to prevent the interaction of the 'culprit' cycle length (storm origin COI) with the other arrhythmic, participants during VT storm (refractoriness, dispersion of refractoriness, conduction velocity, available circuit, etc.).

The processor 160 analyzes the cardiac signals to identify normal and abnormal episodes, such as VT/VF episodes. When a VT/VF episode is identified, the processors 160 performs a binning operation, based on one or more binning rules, to record the VT/VF episode. At the onset of a ventricular fibrillation or tachycardia episode, one or more events/beats will occur that are not classified as VT or VF. Hence, a variable number of events/beats will not be classified as a VT or VF event. The unclassified events are referred to as "un-binned" events. As the VT or VF episode continues, the processor receives sufficient cardiac signals to classify a VT or VF episode. Once an episode is classified as VT or VF, each subsequent event/beat within the episode is classified as a VT or VF event and is "binned" as a 'TACH' or 'FIB' event. The number of un-binned events, during onset of an episode may vary depending upon the preceding heart rate and the rate of the VT/VF. As one example, the processor may utilize an interval-averaging binning rule to establish an upper limit (e.g., 4 or 5) for the number of un-binned beats during onset of a VT or VF episode. In addition to the un-binned beats, a first beat of a tachycardia, or a precipitating PVC, may be incorrectly binned as a sinus (VS) beat or un-binned depending upon its degree of prematurity. A total number of un-binned events plus any binned (VS) sinus events are collectively treated as arrhythmia transition events and will vary. By way of example, 2 to 5 events may be recorded as un-binned events and/or binned as sinus events during onset of a VT or VF episode. It is recognized that the number of arrhythmia transition events may vary.

In accordance with embodiments herein, the methods and systems account for the un-binned events and binned as sinus events in a manner that does not interfere with identification of a storm origin. The methods and systems also account for a number of AE events varying between patients. The methods and systems also identify VT episodes that emerge from stable rhythms as well as VT episodes that emerge from non-stable rhythms, such as long-short and short-long-short sequences. The systems and methods herein reject early VT events and identify a correct or resultant storm origin rate or interval.

The processor 160 further controls a shocking circuit 117 by way of a control signal. The shocking circuit 117 generates stimulating pulses of low (up to 0.5 Joules), moderate (0.5-10 Joules), or high energy (11 to 40 Joules), as controlled by the microcontroller 10. Stimulating pulses are applied to the patient's heart through at least two shocking electrodes. One or more pulse generators 170 and 172 generate various types of therapy, such as pacing, defibrillation and ATP stimulation pulses for delivery by desired electrodes. The electrode configuration switch 174 (also referred to as a switch bank) controls which terminals 147-152 are connected to the pulse generators 170, 172, thereby controlling which electrodes receive a therapy. The pulse generators, 170 and 172, may include dedicated, independent pulse generators, multiplexed pulse generators, shared pulse generators or a single common pulse generator. The pulse generators 170 and 172 are controlled by the processor 160 via appropriate control signals to trigger or inhibit stimulation pulses. The processor 160 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 174 connects the sensing electronics to the desired terminals 147-52 of corresponding sensing electrodes. For example, a portion of the terminals may be coupled to electrodes configured to define a sensing and/or shocking vector that passes through the left ventricle. The switch 174 may connect terminals to the marker pulse sensing circuit 184 (which corresponds to the marker pulse sensing channel) and the microcontroller. The circuit 184 may amplify, filter, digitize and/or otherwise process the sensed signals from the select electrodes.

The switch 174 also connects various combinations of the electrodes to an impedance measurement circuit 113. The impedance measuring circuit 113 includes inputs to collect multiple measured impedances between corresponding multiple combinations of electrodes. For example, the impedance measuring circuit 113 may collect a measured impedance for each or a subset of the active sensing vectors.

The switch bank 174 includes a plurality of switches for connecting the desired electrodes to the appropriate I/O circuits, thereby providing complete electrode programmability. The switch 174, in response to a control signal from the processor 160, determines the polarity of the stimulation pulses (e.g., unipolar, bipolar, co-bipolar, etc.) by selectively closing the appropriate combination of switches (not specifically shown). The outputs of the sensing circuits 182 and 184 are connected to the processor 160 which, in turn, is able to trigger or inhibit the pulse generators 170 and 172, respectively. The sensing circuits 182 and 184, in turn, receive control signals from the processor 160 for purposes of controlling the gain, threshold, the polarization charge removal circuitry (not shown), and the timing of any blocking circuitry (not shown).

Cardiac signals are also applied to the inputs of an analog-to-digital (A/D) data acquisition system 190. The data acquisition system 190 is configured to acquire intracardiac electrogram signals, convert the raw analog data into a digital signal, and store the digital signals for later processing and/or telemetric transmission to an external device. The data acquisition system 190 samples cardiac signals across any pair of desired electrodes. The data acquisition system 190 may be coupled to the processor 160, or other detection circuity, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract.

The processor 160 is further coupled to a memory 194 by a suitable data/address bus 196. The memory 194 stores cardiac signals, programmable operating, impedance measurements, impedance derivation and therapy-related parameters used by the processor 160. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart.

The operating and therapy-related parameters may be non-invasively programmed into the memory 194 through a telemetry circuit 100 in telemetric communication with the external device, such as a programmer, trans-telephonic transceiver, or a diagnostic system analyzer. The telemetry circuit 100 is activated by the processor 160 by a control signal. The telemetry circuit 100 advantageously allows intracardiac electrograms and status information relating to the operation of the IMD 110 (as contained in the processor 160 or memory 194) to be sent to an external device 101 through an established communication link 103. The memory 194 stores cardiac signals such as EGMs in connection with paced events and sensed events.

The IMD 110 may include a physiologic sensor 107 to adjust pacing stimulation rate according to the exercise state of the patient. The physiological sensor 107 may further be used to detect changes in cardiac output, changes in the physiological condition of the heart, or diurnal changes in activity (e.g., detecting sleep and wake states). The battery 111 provides operating power to all of the circuits shown in FIG. 1.

VT/VF Storm Analysis and Intervention

Figure 2A:
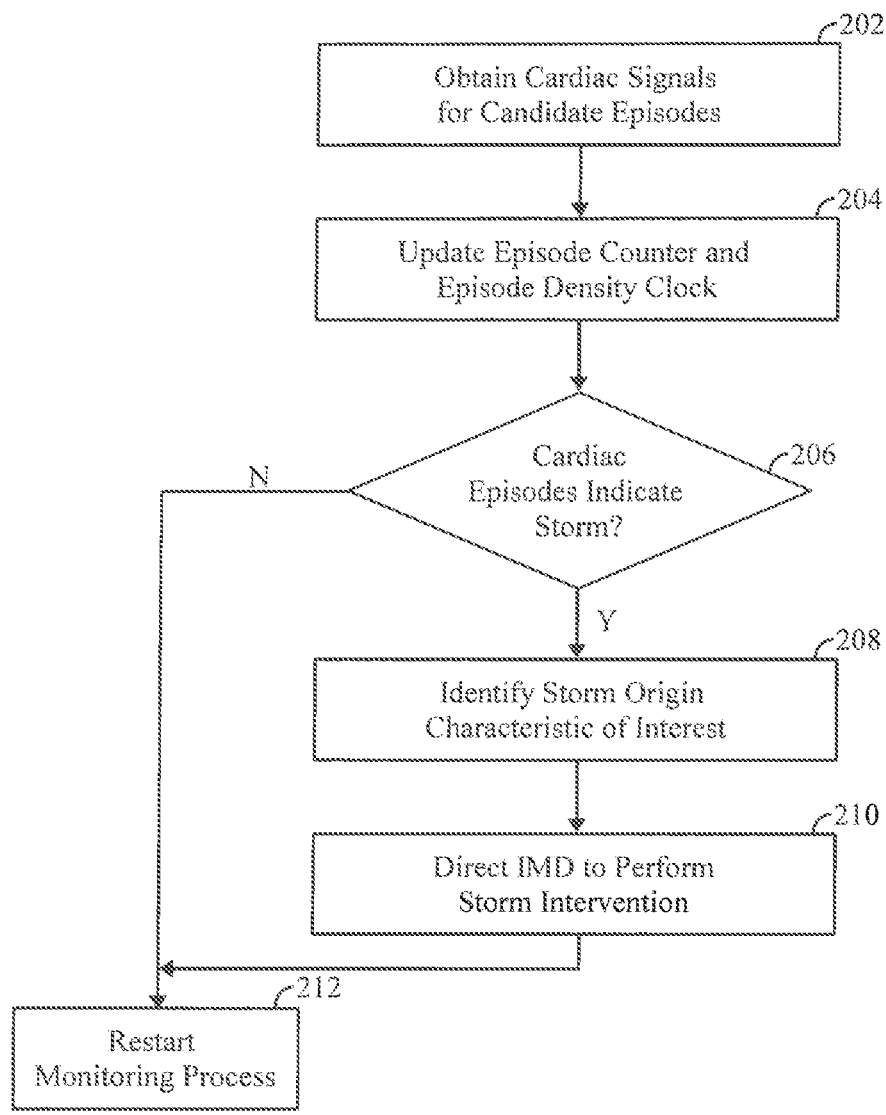
FIG. 2A illustrates a process for detecting VT/VF storm in accordance with embodiments herein.

FIG. 2A illustrates a process for detecting VT/VF storm in accordance with embodiments herein. The process of FIG. 2A may be implemented by one or more processors of an IMD, alone or in combination with one or more processors of an external device, a remote medical server and the like. As explained herein, the process of FIG. 2A may be initiated in connection with detection, by the IMD, of at least one of a series of VT episodes and/or VF episodes, that represent candidate episodes to be further analyzed. The operation at 202 represents the beginning of a storm monitoring session.

At 202, one or more processors obtain cardiac signals that comprise candidate episodes over a period of time, the candidate episodes. For example, the cardiac signals may be obtained by measuring, in real time, cardiac signals at one or more sensors coupled to the IMD or located on the IMD (e.g., in connection with a leadless device). As another example, the cardiac signals may be obtained by accessing memory to obtain stored cardiac signals that were measured at an earlier point in time. As another example, the obtaining operation may represent transmitting a request from an external device to an IMD and receiving cardiac signals transmitted from the IMD to an external device, such as in connection with performing the analysis of FIGS. 2A-2C at an external device.

At 204, the one or more processors update an episode count and episode density clock based on the candidate episodes within the period of time. As explained herein, the episode count and density clock are utilized to track the number of VT/VF episodes within a predetermined period of time, to determine a frequency/density of the VT/VF episodes. The VT/VF episodes obtained at 202 and tracked at 204 represent "candidate episodes" as the VT/VF episodes have not yet been determined to indicate a ventricular storm arrhythmia, such as VT storm or VF storm.

At 206, the one or more processors determine whether the candidate episodes are indicative of a ventricular storm arrhythmia based on the episode count and episode density clock. For example, the determination may include determining whether a predetermined number of the VT episodes and/or VF episodes occur within a predetermined period of time. Various examples are provided throughout for the number of VT/VF episodes and time period that may be set for detecting whether candidate episodes indicate a ventricular storm arrhythmia. When the determination at 206 identifies a storm, flow advances to 208. Otherwise, flow moves to 212.

At 208, given that the VT/VF episodes indicate a ventricular storm arrhythmia, next the process seeks to identify the origin of episodes within the storm. At 208, the one or more processors identify a storm origin characteristic of interest preceding onset of the at least a portion of the VT/VF episodes. The storm origin characteristic of interest is determined from one or more events (e.g., sensed events), referred to as storm origin events. The storm origin events precede onset of each of the VT/VF episodes. As explained below in more detail, the storm origin characteristic of interest is determined based on a collection of candidate origin characteristics of interest. As explained below in more detail, for each VT/VF episode, a corresponding candidate origin characteristic of interest is determined. The candidate origin characteristic of interest precedes the corresponding VT/VF episode by a predetermined number of events, also referred to as origin lag. For example, the candidate origin characteristic of interest may precede onset of a corresponding VT/VF episode by a number of events that is programmed by a clinician or automatically determined based on analysis of prior storm arrhythmias. The predetermined number of events may be set at the time of manufacture, programmed at the time of implant and/or updated after implant. Non-limiting examples of the number of events that may be set between the candidate origin characteristic of interest and classification of a VT/VF episode by the device are generally 3-6 events, and more specifically 4-5 events.

At 210, the one or more processors direct the IMD to perform a storm intervention based on the identifying operation. For example, the direction may include directing the IMD to deliver an intervention therapy that is based on the storm origin characteristic of interest. The intervention therapy may represent a pacing therapy having a pacing rate that is based on the storm origin characteristic of interest. The candidate origin characteristic of interest may represent one or more of a beat to beat interval and/or a heart rate. The pacing rate for the intervention therapy may be set to a predetermined amount greater than the beat to beat interval and/or heart rate. As explained hereafter, the pacing rate may be defined in various manners, such as in connection with increasing a heart rate by a predetermined number of events per minute, increasing the heart rate by a predetermined percentage, reducing the beat to beat interval by a predetermined amount of time (e.g., in milliseconds), reducing the beat to beat interval by a predetermined percentage and the like.

Additionally or alternatively, the direction at 210 may include the IMD providing a physical indication to the patient, in which the IMD is implanted. For example, the physical indication may represent an audible or vibratory response produced by the IMD to notify the patient that a VT/VF storm has been identified. Additionally or alternatively, the direction provided by the IMD may include transmitting a storm indication from the IMD to an external device. For example, the external device may represent a home or bedside external monitoring device that wirelessly communicates with the IMD. The home or bedside external monitoring device may communicate over a local area network, wide area network, the Internet or other medium with one or more medical networks, such as one or more servers, workstations or other terminals utilized by a physician or other healthcare provider in connection with monitoring the patient. Once the storm intervention process is completed, flow moves to 212.

At 212, the process for a storm monitoring session may be reset, such as by clearing the episode counter and episode density clock. In accordance with an embodiment, the process may return to 202, where the IMD continues to monitor for new VT and/or VF episodes and begin a new storm monitoring session. When new VT/VF episodes are detected, the operations of 202-210 may be repeated. Optionally, at 212, the IMD may suspend operation of VT or VF therapy, such as to avoid further ventricular tachycardia and ventricular fibrillation shocks. Optionally, the IMD may modify the settings utilized in connection with detecting VT and/or VF, such as by adjusting the rate thresholds utilized during detection to identify VT and/or VF.

Figure 2B:
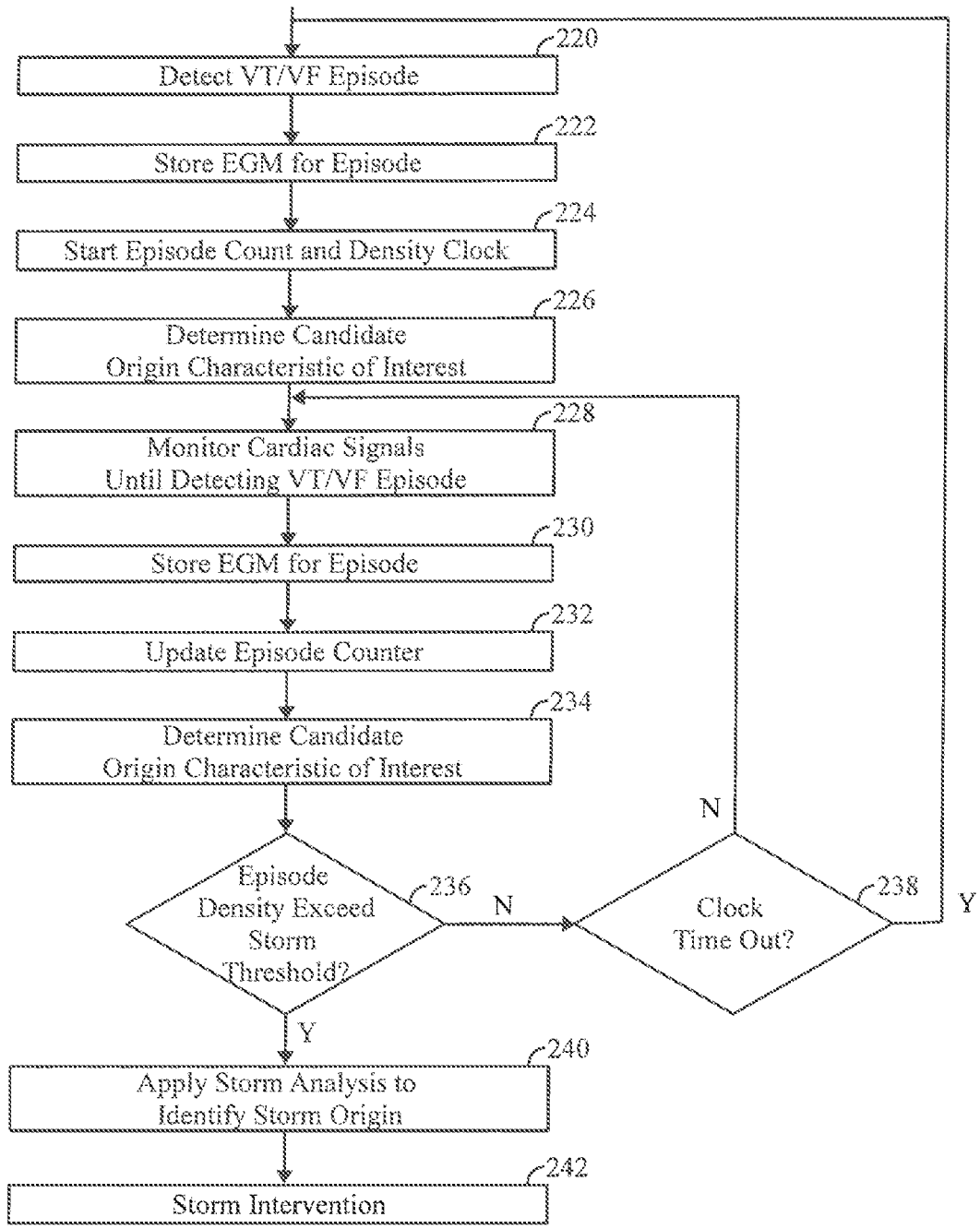
FIG. 2B illustrates a more detailed example of a process for identifying ventricular storm arrhythmias in connection with an embodiment herein.

FIG. 2B illustrates a more detailed example of a process for identifying ventricular storm arrhythmias in connection with an embodiment herein. It is recognized that the operations of FIG. 2B include one example of a more detailed implementation of the general operations described in FIG. 2A. The process of FIG. 2B may be carried out by one or more processors of an IMD, alone or in combination with one or more processors of an external device, a remote medical server and the like.

At 220, the one or more processors detect a VT/VF episode from cardiac signals (collected by sensors of the IMD in real time or at a prior point in time). The operation at 220 represents the beginning of a storm monitoring session, during which the process attempts to determine whether VT/VF episodes occur with sufficient density to warrant characterization as VT/VF storm. For example, the processors may apply conventional ventricular tachycardia and/or ventricular fibrillation detection, discrimination and diagnostic algorithms to analyze sensed cardiac signals. When a VT/VF episode is detected, the IMD applies a programmed treatment (e.g., delivering one or more ventricular tachycardia shocks, applying anti-tachycardia pacing therapy, etc.).

At 222, the one or more processors store the cardiac signals (e.g., electrocardiogram signals) for a capture window associated with the VT/VF episode. The cardiac signals may be stored in memory within the IMD and/or transmitted wirelessly to an external device. The stored cardiac signals are not limited to events occurring after identification or onset of a VT/VF episode. Instead, the stored cardiac signals are for a capture window that includes one or more events (sensed and/or paced) that precede onset of the VT/VF episode. For example, the capture window may be defined by a predetermined period of time that precedes identification or onset of the VT/VF episode. Additionally or alternatively, the capture window may be defined by a predetermined number of events that precede the first event identified as part of the VT/VF episode. The capture window is long enough to include the storm origin event, AE events and the VT/VF episode. Optionally, other storage management rules may be applied to define the length and position of the capture window.

At 224, the one or more processors initiate/start an episode counter and an episode density clock. The episode counter maintains a running count of a number of VT/VF episodes that have occurred since the last time that the episode counter was started/initiated. The episode density clock maintains a running temporal counter to track an amount of time that has lapsed since the start of the clock (corresponding to the detection of a first VT/VF episode in a current storm monitoring session).

At 226, the one or more processors determine a candidate storm origin event and characteristic of interest from the candidate storm origin for the current VT/VF episode. The candidate storm event origin and characteristic of interest may be determined in various manners, as described herein. A candidate storm origin characteristic of interest is saved in memory in connection with a current storm monitoring session. The operation at 226 is discussed below in more detail in connection with FIG. 2C. Optionally, the operation at 226 may be omitted at the present point in the process of FIG. 2B and instead performed at a later point in time (e.g., during storm analysis).

At 228, the one or more processors monitor cardiac signals sensed by the IMD until detecting a next VT/VF episode. The next VT/VF episode may occur a relatively short period of time after the prior VT/VF episode. Alternatively, a relatively long period of time may occur between VT/VF episodes. Optionally, at 228, when the cardiac signals are monitored for a long period of time, a session timer may timeout to cancel the present storm monitoring session of FIG. 2B. When the next VT/VF episode is identified before time out of the timer, flow continues to 230. At 230, the one or more processors store the cardiac signals associated with the next VT/VF episode. At 232, the one or more processors update the episode counter, such as by incrementing a running count of VT/VF episodes that have occurred since starting the present storm monitoring session.

At 234, the one or more processors determine the candidate storm origin event and characteristic of interest associated with the current VT/VF episode identified at 228. A candidate storm origin characteristic of interest is saved in memory with previously stored candidate origins for the current storm monitoring session. Optionally, the operation at 234 may be omitted at the present point in the process of FIG. 2B and instead performed at a later point in time (e.g., during storm analysis).

At 236, the one or more processors determine whether the episode density exceeds a storm threshold. For example, the one or more processors may compare the episode count to a threshold. When the episode count exceeds the threshold, flow advances to 240. At 240, the one or more processors apply a storm analysis, discussed below in more detail. The storm analysis, among other things, identifies a storm origin characteristic of interest from the candidate storm origin characteristics of interest determined at 226 and 234. At 242, the one or more processors perform storm intervention, as discussed herein in more detail.

Returning to 236, when the episode count does not exceed the threshold, flow moves to 238. At 238, the one or more processors determine whether the density clock has timed out. For example, a maximum time period maybe set during which VT/VF episodes are to be counted during any single storm monitoring session. When the predetermined minimum numbers of VT/VF episodes are not counted during the maximum time period, the density clock times out and flow returns to 220. When the density clock has not yet timed out at 238, flow returns to 228. The operations at 228-238 are repeated until either the episode density exceeds the storm threshold or the density clock times out. Thereafter, the storm monitoring session ends. Optionally, the operations at 236 and 238 may be replaced by an alternative analysis to determine whether the candidate VT/VF episodes indicate a ventricular storm arrhythmia.

In the foregoing example, operations are described in connection with 226 and 234, in which candidate origin characteristics of interest are determined before declaring a set of VT/VF episodes to correspond to a ventricular storm arrhythmia. Alternatively, the operations at 226 and 234 may be omitted entirely from the process of FIG. 2B. Instead, the determination of the candidate storm origin characteristics of interest for each of the VT/VF episodes may be determined during the storm analysis at 240 after declaring a set of VT/VF episodes to correspond to a ventricular storm arrhythmia.

Figure 2C:
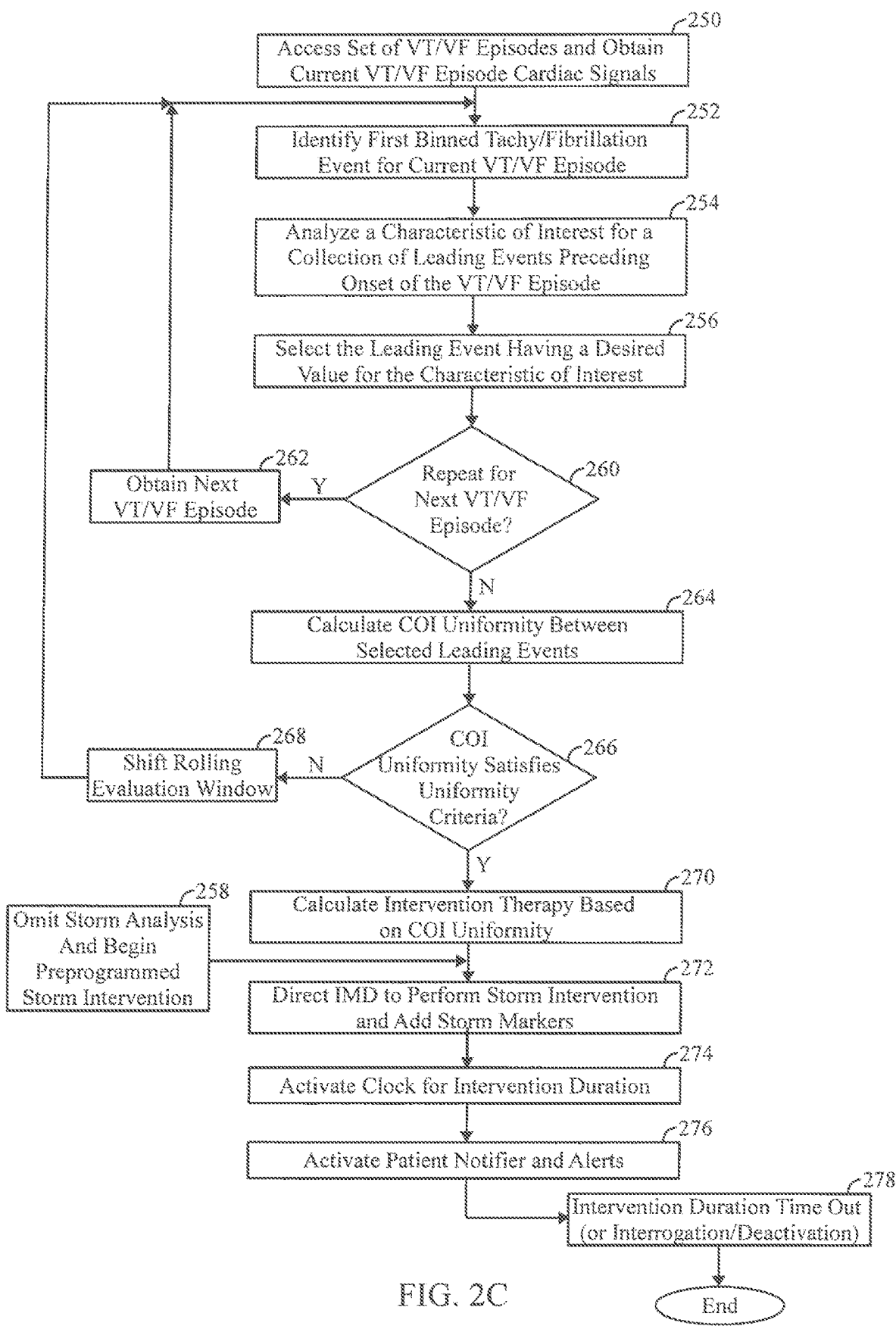
FIG. 2C illustrates the process for applying a storm analysis and intervention in accordance with embodiments herein.

FIG. 2C illustrates the process for applying a storm analysis in accordance with embodiments herein. At 250, the one or more processors access a set of VT/VF episodes collected in connection with a storm monitoring session. The one or more processors obtain cardiac signals for a current VT/VF episode from the set of VT/VF episodes. For example, the analysis of FIG. 2C may be performed by the IMD during or immediately after providing a therapy in connection with a most recent VT/VF episode. The set of VT/VF episodes may be collected immediately prior to the analysis of FIG. 2C or at an earlier point in time (e.g., several minutes, a few hours, or days). For example, the set of VT/VF episodes may have occurred at an earlier point in time, but are being analyzed, during a time at which the IMD is performing no other operation, such as when the patient is not experiencing an arrhythmia, is asleep or otherwise. As another example, the process of FIG. 2C may be performed one or more months after collection of the set of VT/VF episodes, such as when performing the storm analysis as a post processing operation. The post processing operation may be performed by the IMD, by a home or bedside monitor, by a remote server or other computing device.

For example, nightly the IMD may transmit to a remote server any arrhythmic activity experienced during the prior 24 hours. The remote server may then perform a storm analysis of FIG. 2C.

At 252, the one or more processors identify, in connection with a current VT/VF episode, a first binned Tachy/fibrillation event therein. The first binned Tachy/fibrillation event represents the first event classified as a tachycardia or fibrillation event, which corresponds to onset of the tachycardia/fibrillation episode.

At 254, the one or more processors analyze one or more characteristics of interest (COI) for a collection of "leading" events that immediately precede onset of the tachycardia/fibrillation episode. The leading events represent potential candidate storm origins, as the leading events may contribute one or more factors to onset of the VT/VF episode. The collection of leading events extends backward in time to precede onset of the VT/VF episode by a predetermined number of events or by a predetermined time period. The collection of leading events may extend over a time period sufficient to cover the origin lag. Continuing with this example, when the origin lag is expected to be up to 6 events, at 254, the collection of leading events, for which the COI is analyzed, may include at least the 6 events preceding the first binned TACH/FIB event. By way of example, the characteristic of interest may represent the beat to beat interval or the heart rate. Thus, when analyzing 6 leading events, the process identifies 6 beat to beat intervals and/or 6 heart rates, representing 6 candidate storm origin characteristics of interest.

At 256, the one or more processors select a leading event, from the collection, that has a desired value for the characteristic of interest. For example, when the characteristic of interest represents the beat to beat interval, the identification at 256 may select the leading beat having the longest beat to beat interval from the collection. Alternatively, at 256, a leading event may be selected based on some other aspect of the beat to beat interval (e.g., closest to the average interval). Alternatively, the leading event, from the collection, may be selected based on an aspect of the heart rate, such as the fastest, average or slowest heart rate.

At 260, the one or more processors determine whether additional VT/VF episodes exist within the collection to be analyzed. When additional VT/VF episodes exist, flow moves to 262 where the next VT/VF episode is obtained. Thereafter, flow returns to 252 and the operations at 252 to 256 are repeated. Alternatively, at 260, when it is determined that all of the VT/VF episodes in the collection have been analyzed, flow moves to 264.

At 264, the one or more processors calculate a uniformity of the one or more characteristics of interest between the selected leading events analyzed thus far. For example, when 10 VT/VF episodes are analyzed, COI uniformity is determined for the selected leading event (storm origin event) from each of the 10 VT/VF episodes. For example, the uniformity of the beat to beat interval may be determined. The uniformity may be characterized in various manners, such as based on a mean (± a range of deviation from the mean) between the beat to beat intervals for the selected leading events.

At 266, the one or more processors determine whether the uniformity calculated at 264 satisfies a uniformity criterion. For example, the uniformity criteria may represent an upper limit for the range over which the selected leading events vary from the mean. Additionally or alternatively, the uniformity criteria may correspond to a difference between the minimum and maximum intervals for the selected leading edges (e.g., the longest and shortest intervals are within X milliseconds of one another). Additionally or alternatively, the uniformity criteria may correspond to a heart rate below a specified cutoff. Optionally, the uniformity criteria may simply correspond to a minimum number of VT/VF episodes to be analyzed. For example, determination at 266 may require that at least 5 (or some other number of) VT/VF episodes be analyzed to determine the COI uniformity. Additionally or alternatively, the uniformity criteria may be defined in connection with other mathematical factors defining the distribution of the characteristic of interest from the selected leading events. When the uniformity satisfies the uniformity criteria, flow moves to 270. Otherwise, flow moves to 268.

At 268, the one or more processors shift a rolling evaluation window forward to include one or more additional VT/VF episodes. The rolling evaluation window may include the most recent X number of VT/VF episodes. For example, at each iteration through 268, the rolling evaluation window may be shifted forward one new VT/VF episode. Alternatively, the rolling evaluation window may be shifted forward to include a completely new collection of VT/VF episodes. Alternatively, the rolling evaluation window may be shifted forward to include a portion of the VT/VF episodes already analyzed and a new group of VT/VF episodes.

At 270, the one or more processors calculate an intervention therapy based on the storm origin COI. For example, the intervention therapy may be defined, at least in part, by a pacing rate, that is set based on the beat to beat interval (representing the storm origin characteristic of interest). Optionally, the pacing rate may be set based on a heart rate that is determined as the storm origin characteristic of interest. The relation between the intervention therapy and the storm origin characteristic of interest may vary. The relation between the intervention therapy (e.g., pacing rate) and the storm origin may be defined as a percentage or as an absolute increase/decrease. For example, a pacing rate for an intervention therapy may be set to be a predetermined amount greater than the heart rate identified as the storm origin characteristic of interest. As another example, the pacing rate for the intervention therapy may be set to have a beat to heat interval that is a predetermined time less than the beat to beat interval identified as the storm origin characteristic of interest.

At 272, the one or more processors direct the IMD to perform a storm intervention based on the storm origin characteristic of interest. When the intervention represents delivery of an intervention therapy, the IMD activates an intervention pacing rate (as calculated at 270). Additionally or alternatively, a maximum intervention rate limit may also be set and implemented at 272.

In accordance with embodiments herein, an implantable medical device (IMD) implements a VT storm intervention therapy, in which a select pacing rate is applied for a selected duration, such as 20 events per minute faster, or 20 percent faster than the identified storm origin cycle length. A maximum (capped) intervention heart rate may be selected by the physician in light of known cardiac factors (e.g., 100-120 events per minute). The storm intervention therapy is applied until time out of a select duration or the therapy is deactivated during a programmer session. The IMD may produce various outputs in connection with a storm intervention process. For example, the IMD may provide, as an output, an activation of a patient vibratory notification and/or transmit an alert to a bedside monitoring system (e.g., the Merlin.NET™ network) to prompt the patient to seek medical attention for management of the storm episodes.

A VT storm intervention therapy may represent an emergency strategy with multiple physician-selected parameters and boundaries of scale. The emergency strategy may be applied when analysis of the current VT storm confirms that the storm origin characteristic represents a treatable onset mechanism.

At 274, the one or more processors activate a clock associated with an intervention duration. The intervention therapy is delivered until the intervention duration clock times out. In addition, at 274, the one or more processors begins to add storm related markers to the real-time display (and recordings) of the cardiac signals. At 276, the one or more processors activate a patient notifier and/or other alerts. For example, the patient notifier may provide a physical indication to a patient having the IMD, such as providing an audible or vibratory notification. Additionally or alternatively, the IMD may transmit a storm indicator to an external device, such as a home or bedside monitor device.

At 278, the one or more processors determine whether the intervention duration clock has timed out, whether a patient notifier clock has timed out, and/or whether an external device is interrogating the IMD. As another example, at 278, the processors may determine whether an external device has instructed the IMD to deactivate one or more aspects of the functionality of the IMD related to storm intervention and/or related to the treatment of VT/VF episodes.

Optionally, the process of FIG. 2C may be initiated at 258, skipping the operations at 250-270. For example, in certain circumstances, it may be determined to omit/forgo the storm analysis to identify a COI uniformity and/or storm origin COI. Instead, it may be desirable to begin storm intervention with physician preprogrammed intervention therapy parameters once a ventricular storm arrhythmia has been declared in connection with the operations of FIGS. 2A and/or 2B.

For example, with reference to FIG. 2B, once it is determined at 236 that the episode density is sufficient to declare a ventricular storm arrhythmia, the process may skip the storm analysis at 240 and move directly to the storm intervention at 242. When doing so, the operations of FIG. 2C at 250-270 are skipped and instead flow begins at 258. At 258, one or more physician preprogrammed parameters are identified for an intervention therapy. Thereafter, flow advances to 272-278 as explained above, where the storm therapy is delivered for a predetermined duration, as well as providing a patient notifier and transmitting a storm indication to an external device.

Example Onset Event Patterns

Figure 3A:
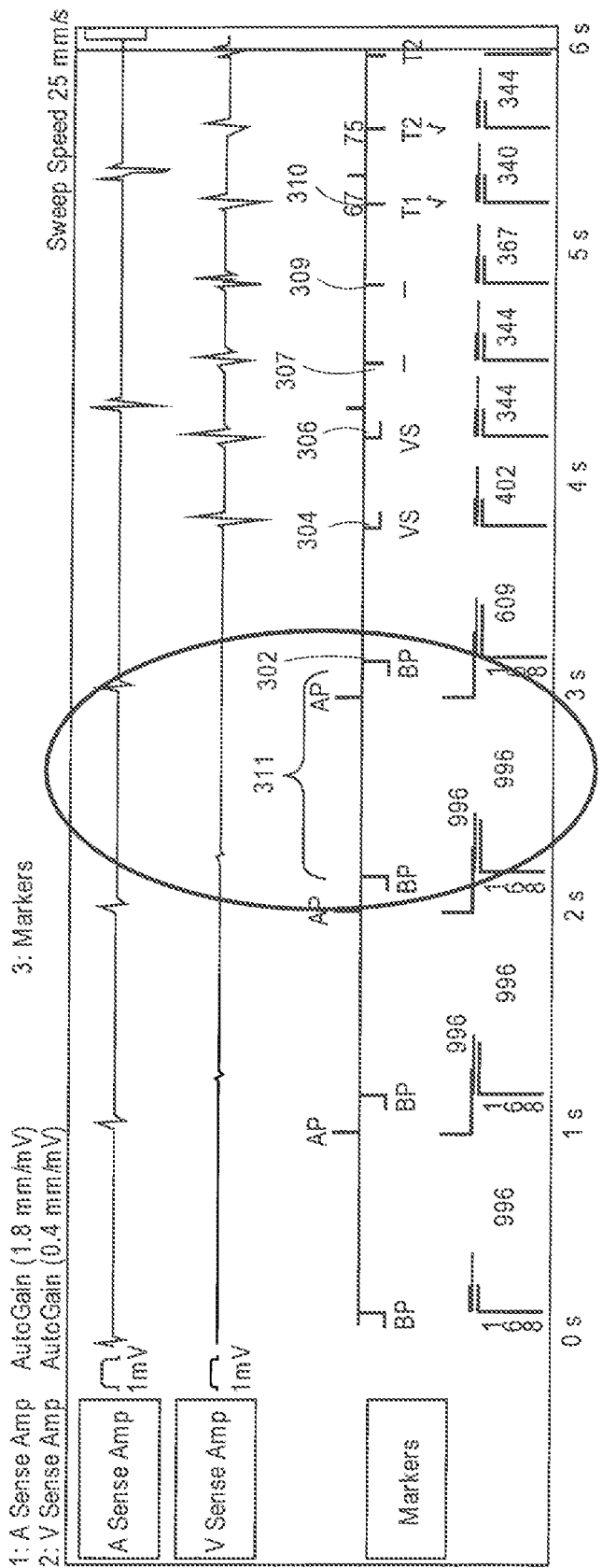
FIG. 3A illustrates an example of atrial and ventricular cardiac signals that are collected by an IMD during a VT storm exhibiting a first type of storm onset events in accordance with an embodiment herein.

Next, examples will be discussed in connection with FIGS. 3A-3H regarding alternative storm onset beat patterns that may occur preceding a first tachycardia or fibrillation binned event. The relative frequency of each of the variations in binned events is described below. The methods and systems described herein may be modified based on a number of leading events, before the first TACH or FIB binning event, that may potentially represent a storm origin and include a storm origin COI. FIG. 3A illustrates an example of atrial and ventricular cardiac signals that are collected by an IMD during a VT episode exhibiting a first type of storm onset events in accordance with an embodiment herein. In FIG. 3A, a "monomorphic" VT episode emerges from a stable preceding rhythm and a relatively late coupled PVC. The storm origin, representing a pre-tachycardia cycle of interest, is circled. It is recognized that, while the circle covers two markers denoted "BP", the second BP marker 302 following the 996 msec, delay corresponds to the BP cardiac event that occurred after the 996 msec, delay. Accordingly, in the following examples, the later marker 302 within the circle corresponds to the storm origin. The storm origin corresponds to an interval of 996 msec, between successive biventricular paced (BP) events. A first TACH binned event 310 is denoted as T1, and is preceded by 2 un-Shinned events 307, 309 (denoted with "-" symbols) and by 2 tachycardia events 304, 306 binned as sinus events (denoted as VS). In the example of FIG. 3A, four storm onset events 304, 306, 307, 309 precede the first binned TACH event. In accordance with embodiments herein, methods and systems identify the first TACH event, reject the four prior storm onset events 304, 306, 307, 309, and identify and measure the target interval 311 within the circle.

Figure 3B:
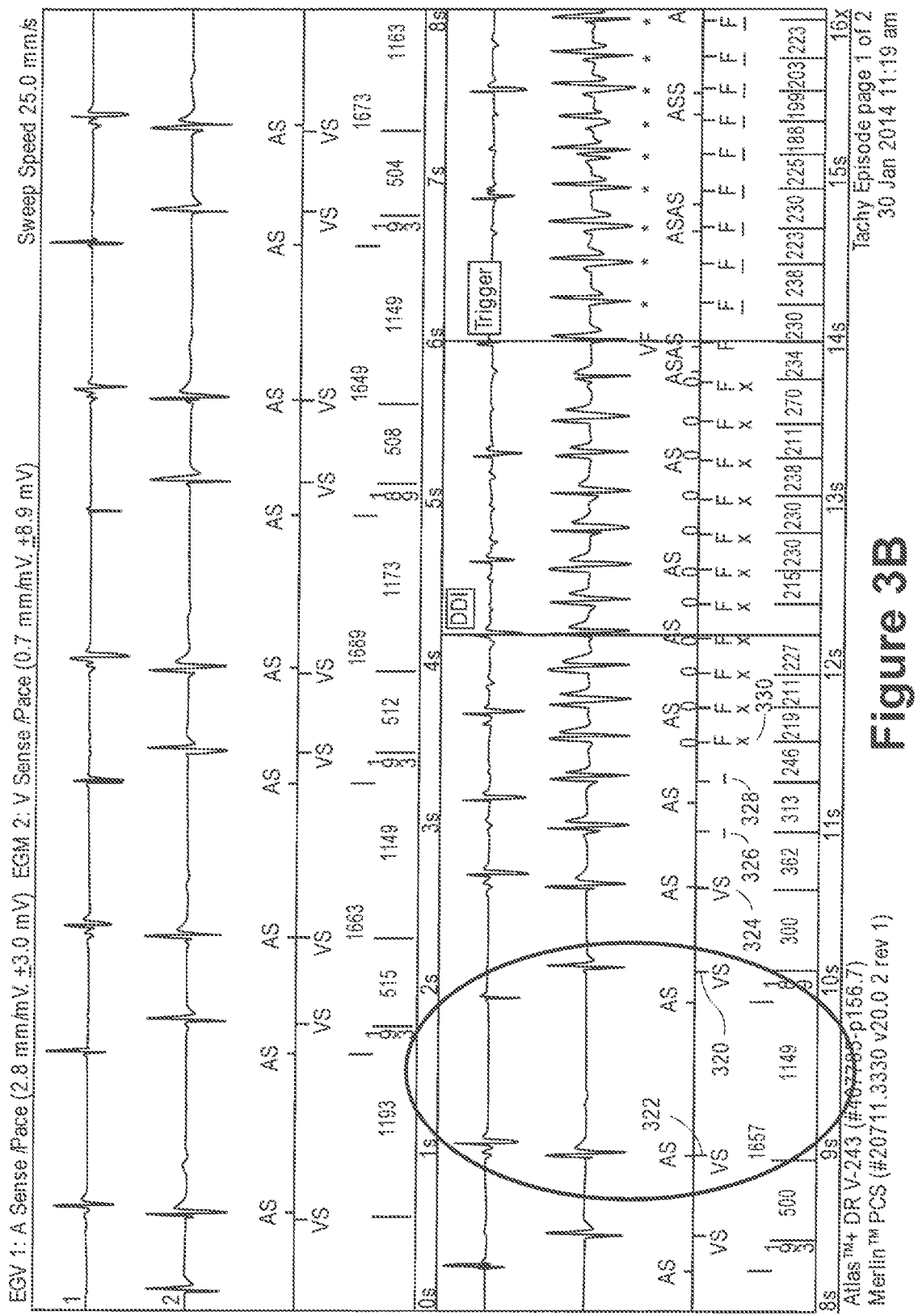
FIG. 3B illustrates an example in which a VF storm is preceded by cardiac signals that exhibit a short-long-short cycle pattern.

FIG. 3B illustrates an example in which a VF episode is preceded by cardiac signals that exhibit a short-long-short cycle pattern. Within the SLS cycle pattern, the storm origin 320 is circled to indicate the beat to beat interval between a pair of VS events 320, 322 separated by a duration of 1148 msec. The storm origin 320 is followed by a VS event 324 and two 'un-binned' events 326, 328, before a first fibrillation (FIB) event 330 is classified/binned. In the example of FIG. 3B, 3 cardiac events occur between the storm origin 320 and the first FIB binned event 330. Thus 3 cardiac event cycles before the first FIB binned event 330 need to be rejected to identify and measure the correct target interval (the interval between 322 and 320) (storm origin).

Figure 3C:
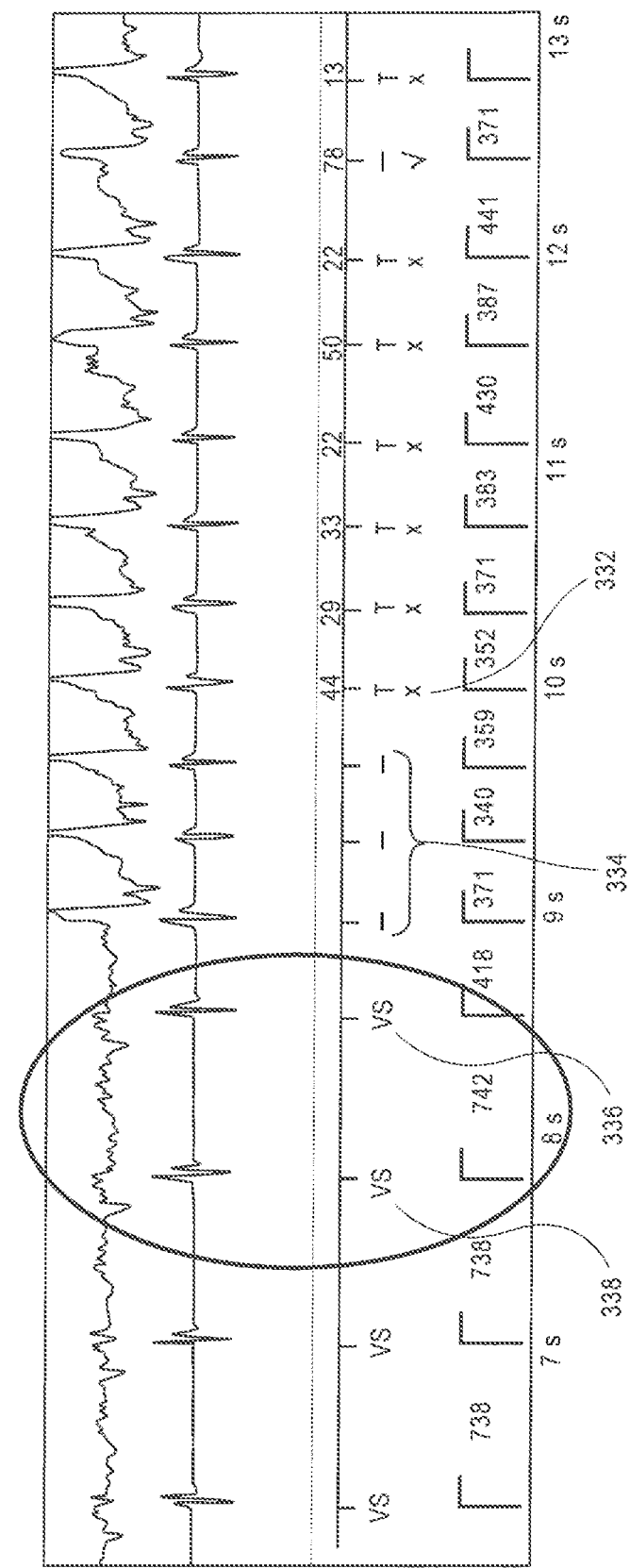
FIG. 3C illustrates an example in which a VT storm is preceded by stable rhythm (no LS, or SLS sequences).

FIG. 3C illustrates an example in which a VT episode is preceded by stable rhythm (no LS, or SLS sequences). The first "TACH" binned event 332 occurs after 3 un-binned tachycardia events 334. The target interval for the storm origin 336 is circled. Three events before first TACH binned event 332 need to be rejected to isolate and measure the target interval for the storm origin 336 (the interval between 338 and 336).

Figure 3D:
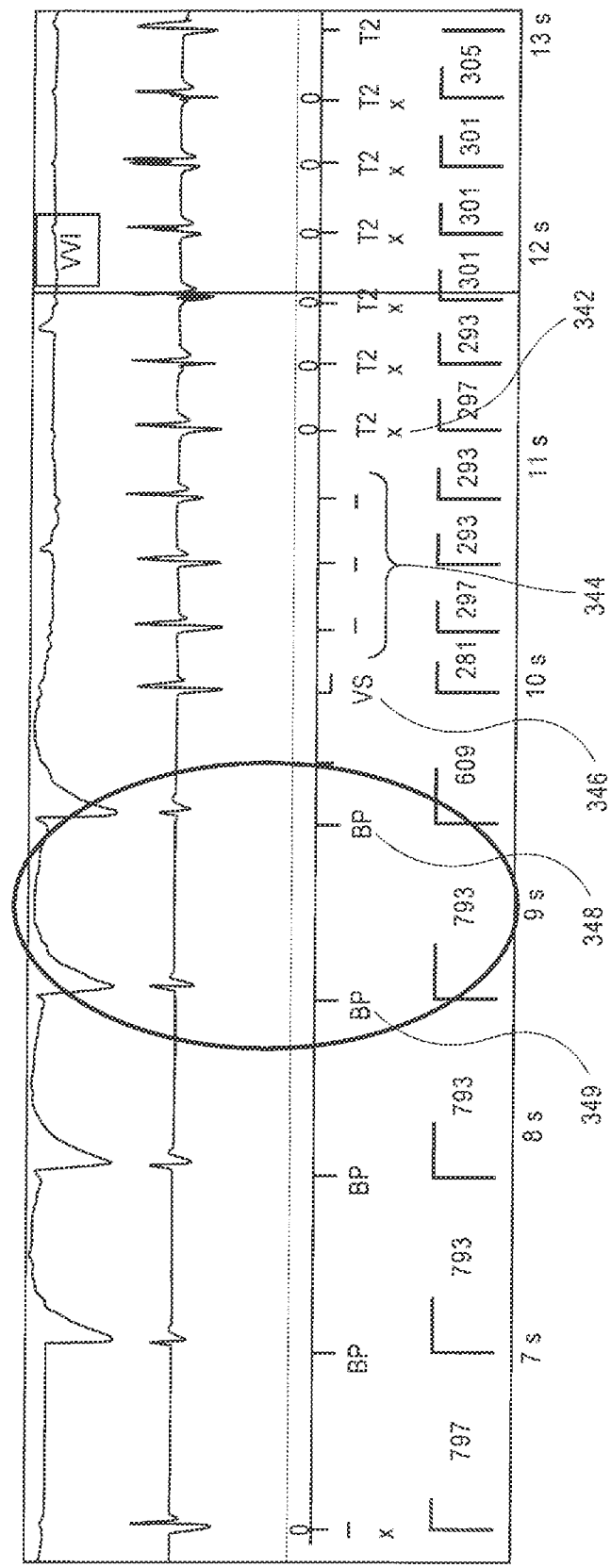
FIG. 3D illustrates an example in which a VT storm emerges from a stable rhythm.

FIG. 3D illustrates an example in which a VT episode emerges from a stable rhythm. The storm origin 348 followed by a binned as sinus event 346 and 3 un-binned events 344 before detection of the first TACH binned event 342. Thus, 4 events occur between the storm origin 348 and the storm onset event (TACH binned event 342). In accordance with methods and systems herein, the events 344, 346 before the first TACH binned event 342 are rejected to identify and measure the target interval for the storm origin 348 (the interval between events 349 and 348).

Figure 3E:
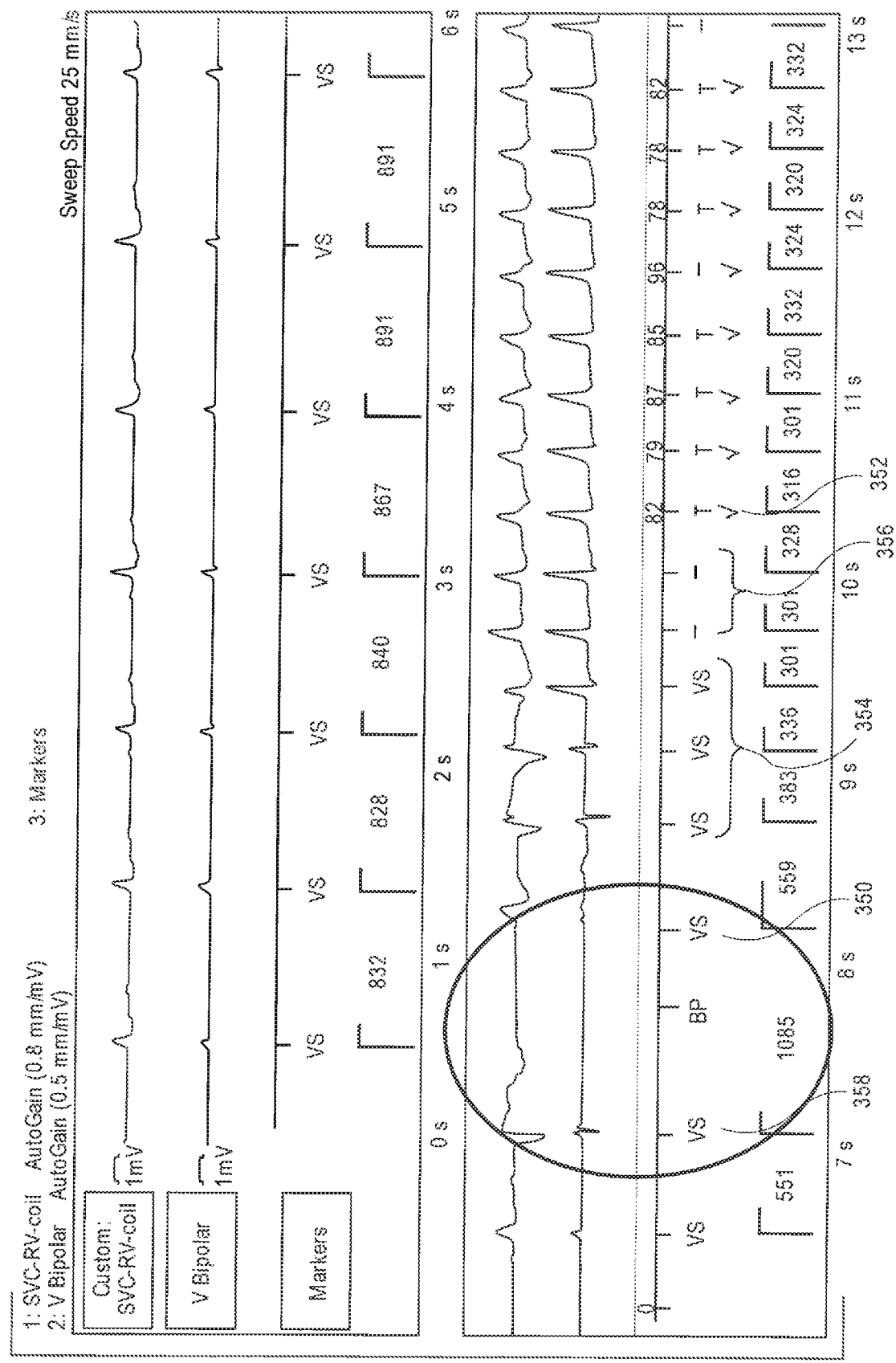
FIG. 3E illustrates an example in which a VT storm emerges from a stable rhythm that has a short-long-short sequence.

FIG. 3E illustrates an example in which a VT episode emerges from a stable rhythm that has a short-long-short sequence. The storm origin 356 that corresponds to the contributory target interval is circled. The first TACH binned event 350 is preceded by 3 binned-as-sinus events 354 and then 2 un-binned events 352 before first TACH binned events 350, providing a total of 5 events before first binning as TACH Thus 5 events preceding the first TACH binned event 350 need to be rejected to isolate the target interval (interval between events 358 and 356)

Multiple VT and VF episodes with different binning behaviors are illustrated in FIGS. 3A-3E. The methods and systems herein determine a methodology for 'rejecting' the initial VT or VF events and capture the storm origin (pre-tachycardia heart rate or pause duration) to which the intervention rate increase is to apply. As an example, in 30 episodes (86%) there were a total of 3 or 4 tachycardia events before the first binned TACH or FIB event (total=un-binned+'binned-as-sinus' events). For correct identification of the heart rate or pause duration preceding the onset of tachycardia, 3 or 4 early events of the tachycardia were rejected, and the preceding beat to beat interval 'accepted' and measured. In these examples where the total number of events to be rejected is 3 or 4, one way of identifying the target interval (storm origin) is to extract the longest interval of the 5 events preceding the first TACH or FIB binned event. In 5 other episodes, cardiac signals of the first TACH or FIB binned event occurred after 5 (or more) events of the VT episode. In the 5 episodes, the rhythm was VT not VF. The VT began at slower rates than the VT detect rate (and were thus labelled VS). In one of the episodes a short-long-sequence contributed to the appearance of 5 events before first VT binned event. Therefore, in accordance with embodiments, 6 cardiac cycles are analyzed for the candidate origin before the first TACH or FIB binned event from stored EGMs, and extraction of the longest interval (COI) from the 6 cycles (leading events) as the storm origin COI (contributing/target preceding heart rate or pause).

Once the pre-VT rate is determined as the storm origin COI, the methods and systems herein apply a pacing rate increase to the pre-VT rate. Optionally, physicians may select an upper limit for the pacing intervention rate. By way of example, the upper limit may be 90, 100 or perhaps up to 130 events per minute, Rolling Window Episode Analysis In accordance with embodiments herein, the VT STORM ANALYSIS may be applied to a collection of X VT/VF episodes once the number of VT/VF episodes reaches X number of episodes within Y amount of time. In the present example, only the first X number of episodes are analyzed and utilized in establishing the parameters for VT STORM INTERVENTION. However, patients experiencing VT storm may not qualify for STORM INTERVENTION during the first collection of VT/VF episodes (e.g., first 6 episodes of VT). Instead, the patient may subsequently 'settle into' a qualifying pattern of VT or VF onset. In such instances, analysis of the first 6 episodes along would not result in a determination to provide storm intervention.

Optionally, the methods and systems herein may be utilized with a rolling evaluation window. Accordingly, the episode analysis of FIGS. 2A-2C continues for a 'rolling window' of X VT/VF episodes. When any X number of consecutive episodes of VT or VF satisfy the 'uniformity of onset' criteria, then VT/VF storm intervention is applied. The rolling window allows a greater number of VT/VF storms to be examined to assess.

In the foregoing embodiments, the algorithms have been described in terms of VT STORM ANALYSIS followed by VT STORM INTERVENTION. However, in some instances, it may be desirable to apply VT STORM INTERVENTION without applying VT STORM ANALYSIS. For example, when patients experience particular types of VT (e.g., Torsades and Brugada syndrome arrhythmias) it may be desirable to apply a predetermined intervention therapy to prevent VT recurrence and to terminate VT/VF storm. For example, a physician may set an IMD for a patient experiencing Brugada, to utilize an intervention therapy having a pacing rate that is increased 20% over the patients normal pacing rate to interrupt VT storm. In Torsades storm, acutely increasing the rate for prevention of recurrence is now a Class IA indication.

Accordingly, in an alternative embodiment, physicians may be afforded an option to empirically increase the heart rate via pacing when VT storm develops in patients known to have these very evidently rate related arrhythmic substrates (Brugada and Torsades). To that end, physicians may be provided with the option upon establishing VT storm, to apply VT STORM ANALYSIS, or progress directly to VT STORM INTERVENTION.

External Device

Figure 4:
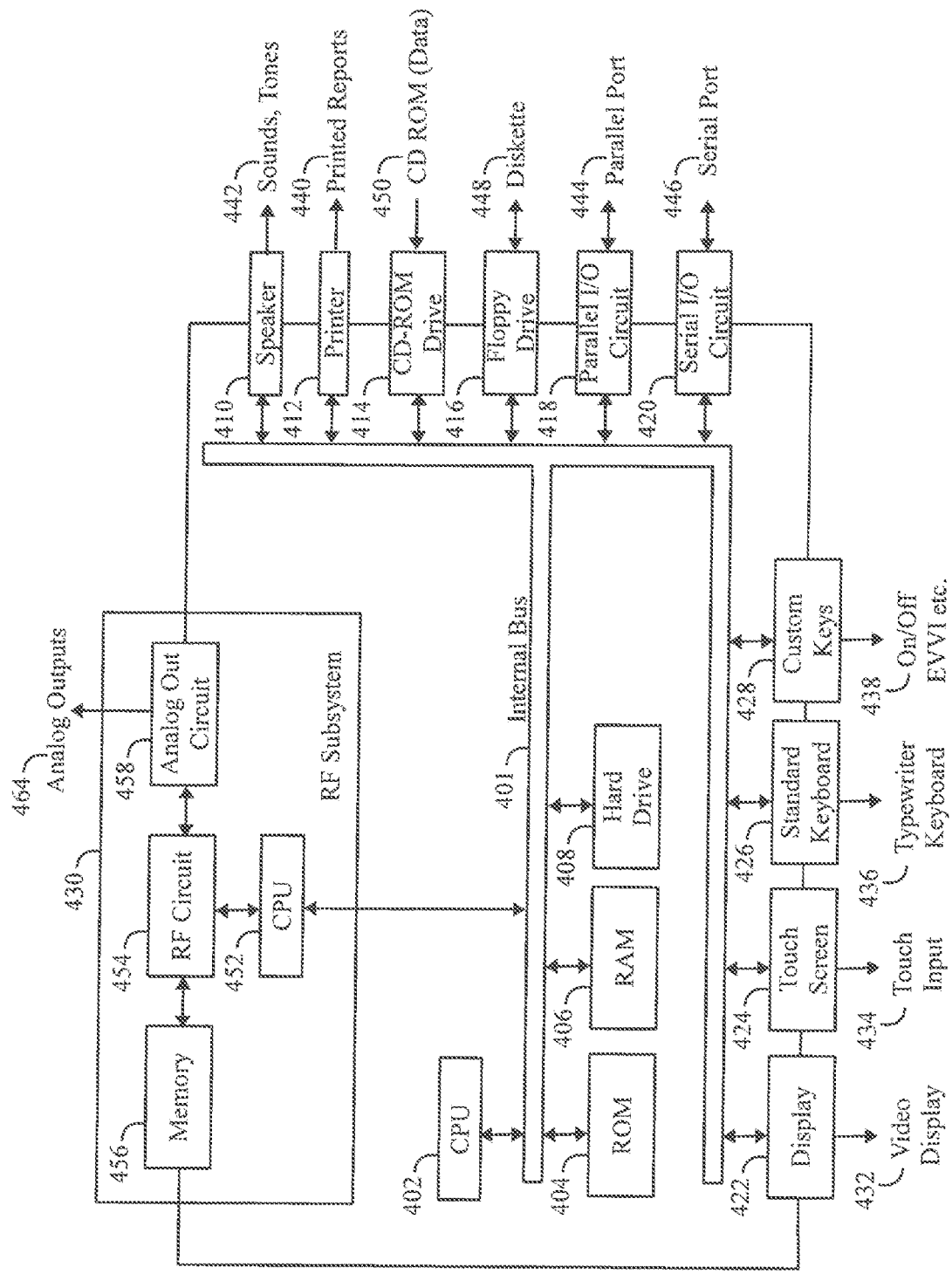
FIG. 4 illustrates a functional block diagram of an external device that is operated in accordance with embodiments herein.

FIG. 4 illustrates a functional block diagram of an external device 401 that is operated in accordance with embodiments herein. The external device 401 may be a workstation, a bedside or home monitoring device (e.g., the Merlin@home™ monitoring device), a portable computer, a tablet computer, a smart watch, an IMD programmer, a PDA, a cell phone and/or the like. The external device 401 may represent a server at a remote medical network.

The CPU 402 typically includes a microprocessor, a micro-controller, or equivalent control circuitry, designed specifically to control interfacing with the external device 401 and with the IMD. The CPU 402 may include RAM or ROM memory, logic and timing circuitry, state machine circuitry, and I/O circuitry to interface with the IMD. The CPU 402 may perform some or all of the operations described in connection with obtaining and analyzing VT/VF episodes for an indication of ventricular storm arrhythmia. The CPU 402 may perform some or all of the operations described in connection with performing storm analysis to identify candidate storm events, resultant storm events, as well as storm characteristics of interest. The CPU 402 may perform some or all of the operations described in connection with determining storm intervention therapy. The CPU 402 may perform some or all of the operations described in connection with determining whether to skip the storm analysis and instead apply a physician defined storm intervention therapy, the parameters for which are defined by the physician and not automatically set based on one or more characteristics of interest from storm origin events.

The external device 401 may include an internal bus 401 that may connect/interface with a Central Processing Unit ("CPU") 402, ROM 404, RAM 406, a hard drive 408, a speaker 410, a printer 412, a CD-ROM drive 414, a floppy drive 416, a parallel I/O circuit 418, a serial I/O circuit 420, the display 422, a touchscreen 424, a standard keyboard 426, custom keys 428, and an RF subsystem 430. The internal bus 401 is an address/data bus that transfers information between the various components described herein. The hard drive 408 may store operational programs as well as data, such as stimulation waveform templates and detection thresholds.

The display 422 (e.g., may be connected to the video display 432). The display 422 displays various information related to the processes described herein. The touchscreen 424 may display graphic information relating to the IMD and include a graphical user interface. The graphical user interface may include graphical icons, scroll bars, buttons, and the like which may receive or detect user or touch inputs 434 for the external device 401 when selections are made by the user. Optionally the touchscreen 424 may be integrated with the display 422. The keyboard 426 (e.g., a typewriter keyboard 436) allows the user to enter data to the displayed fields, as well as interface with the RF subsystem 430. Furthermore, custom keys 428 turn on/off 438 (e.g., EVVI) the external device 401. The printer 412 prints copies of reports 440 for a physician to review or to be placed in a patient file, and the speaker 410 provides an audible warning (e.g., sounds and tones 442) to the user. The parallel I/O circuit 418 interfaces with a parallel port 444. The serial I/O circuit 420 interfaces with a serial port 446. The floppy drive 416 accepts diskettes 448. Optionally, the serial I/O port may be coupled to a USB port or other interface capable of communicating with a USB device such as a memory stick. The CD-ROM drive 414 accepts CD ROMs 450. One or more scanning schedules are stored in the RAM 406, ROM 404, on a CD ROM 450, or elsewhere.

The RF subsystem 430 includes a central processing unit (CPU) 452 in electrical communication with an RF circuit 454, which may communicate with both the memory 456 and an analog out circuit 458. The analog out circuit 458 includes communication circuits to communicate with analog outputs 464. The external device 401 may wirelessly communicate with the IMD and utilize protocols, such as Bluetooth, Bluetooth low energy, MICS, and/or the like. For example, the memory 456, ROM 404, and/or RAM 406 may include Protocol firmware, which is accessed by the CPU 452 and/or 402. The protocol firmware provides the wireless protocol syntax for the CPU 452 and/or 402 160 to assemble data packets, establish communication links, and/or partition data received from the IMD. The RF subsystem 430 and CPU 452 enter scanning states and establish communication sessions as described herein.

In the foregoing examples, the characteristic of interest is described in connection with beat to beat interval and heart rate. Optionally, the characteristic of interest may correspond to AV timing, refractory period, post ventricular atrial refractory period and the like. Optionally, the characteristic of interest may include a combination of characteristics.

In the foregoing examples, the storm analysis identifies a single event as the storm origin event from each VT/VF episode. Optionally, the storm analysis may identify a set of two or more events as storm origin events for a single VT/VF episode. For example, the storm analysis may identify, from a group of 6-10 leading events, 2 or more successive events that have a highest average beat to beat interval or heart rate. Optionally, the storm analysis may identify other characteristics of interest from 2 or more successive events within a group of leading events. The characteristic(s) of interest are then used to automatically define a storm intervention.

Closing Statements

It should be clearly understood that the various arrangements and processes broadly described and illustrated with respect to the Figures, and/or one or more individual components or elements of such arrangements and/or one or more process operations associated of such processes, can be employed independently or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for treating cardiac ventricular storm disorder in a patient under control of one or more processors within an implantable medical device (IMD), comprising:
   obtaining cardiac signals that comprise candidate episodes over a period of time;
   updating an episode count and episode density clock based on the candidate episodes within the period of time;
   determining whether the candidate episodes are indicative of a ventricular storm arrhythmia based on the episode count and episode density clock;
   identifying a storm origin characteristic of interest preceding onset of the candidate episodes;
   setting a pacing rate of a pacing therapy based on the storm origin characteristic of interest; and
   directing the IMD to perform a storm intervention by delivering the pacing therapy at the pacing rate that is set based on the storm origin characteristic of interest.

2. The method of claim 1, further comprising detecting, as the candidate episodes, at least one of VT episodes or VF episodes.

3. The method of claim 2, wherein the determining operation comprises determining whether a predetermined number of the at least one of VT episodes or VF episodes occur within a predetermined period of time.

4. The method of claim 1, further comprising determining the storm origin characteristic of interest from one or more events that precede onset of the corresponding candidate episodes.

5. The method of claim 4, wherein the one or more events precede onset of the corresponding candidate episodes by a predetermined number of events that is between 3 and 6.

6. The method of claim 1, further comprising, for each candidate episode, determining a candidate origin characteristic of interest preceding the corresponding candidate episode and, for each candidate episode, setting the pacing rate based on the candidate origin characteristic of interest.

7. The method of claim 6, wherein the candidate origin characteristic of interest represents at least one of a beat to beat interval or a heart rate, the pacing rate set based on the at least one of the beat to beat interval or heart rate.

8. The method of claim 1, wherein the storm origin characteristic of interest represents at least one of a beat to beat interval or a heart rate, and wherein the pacing rate is set a predetermined amount greater than the at least one of a beat to beat interval or a heart rate.

9. The method of claim 1, wherein the directing operation includes at least one of i) providing a physical indication to a patient having the IMD or ii) transmitting a storm indication to an external device.

10. The method of claim 1, wherein the storm origin characteristic of interest represents a pause duration for at least one of a long-short sequence or a short-long-short sequence, and wherein the setting comprises setting the pacing rate based on the pause duration based thereon, directing the IMD to deliver the storm intervention.

11. The method of claim 1, wherein the setting further comprises increasing the pacing rate for a select duration when the storm origin characteristic of interest indicates that onset of the ventricular storm arrhythmia occurs from a uniform preceding cycle length.

* * * * *